US012408973B2

(12) United States Patent
Keady et al.

(10) Patent No.: US 12,408,973 B2
(45) Date of Patent: Sep. 9, 2025

(54) ELECTROSURGICAL DEVICES WITH A SINGLE CONDUCTIVE TUBULAR ELEMENT FOR ACCESSING ANATOMICAL STRUCTURES

(71) Applicant: Cook Medical Technologies LLC, Bloomington, IN (US)

(72) Inventors: Fionan Keady, Limerick (IE); Margaret Long, Limerick (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 833 days.

(21) Appl. No.: 17/336,991

(22) Filed: Jun. 2, 2021

(65) Prior Publication Data

US 2021/0282845 A1    Sep. 16, 2021

Related U.S. Application Data

(62) Division of application No. 15/661,670, filed on Jul. 27, 2017, now abandoned.

(Continued)

(51) Int. Cl.
*A61B 18/14* (2006.01)
*A61B 17/00* (2006.01)
(Continued)

(52) U.S. Cl.
CPC ..... *A61B 18/1482* (2013.01); *A61B 2017/00278* (2013.01); *A61B 2018/00482* (2013.01);
(Continued)

(58) Field of Classification Search
CPC ...... A61B 18/1477; A61B 2018/00482; A61B 2018/00553; A61B 2018/1425;
(Continued)

(56) References Cited

U.S. PATENT DOCUMENTS 3,313,293 A    4/1967 Chesebrough et al.
5,221,281 A    6/1993 Klicek
(Continued)

FOREIGN PATENT DOCUMENTS

JP    2002-513652    5/2002
JP    2005-143581 A   6/2005
(Continued)

OTHER PUBLICATIONS

International Search Report and Written Opinion in corresponding International Application No. PCT/US2017/044132, dated Oct. 30, 2017, 16 pages.
(Continued)

*Primary Examiner* — Sean W Collins
(74) *Attorney, Agent, or Firm* — Vivacqua Crane, PLLC

(57) ABSTRACT

An electrosurgical medical device may include a conductive tubular element disposed about an outer surface of an elongate tubular member at a distal portion of the tubular member. The conductive tubular member may be delivered to a treatment site of a gastrointestinal (GI) tract of a patient and electrically activated. While electrically activated, the conductive tubular element may create an opening in a wall of the GI tract and a pseudocyst. After the incision is made, the conductive tubular element may be withdrawn from the treatment site and a drainage device may be positioned in the incision for drainage of the pseudocyst.

14 Claims, 13 Drawing Sheets

Related U.S. Application Data

(60) Provisional application No. 62/368,639, filed on Jul. 29, 2016.

(51) Int. Cl.
*A61B 18/00* (2006.01)
*A61B 18/12* (2006.01)

(52) U.S. Cl.
CPC . *A61B 2018/00601* (2013.01); *A61B 18/1206* (2013.01); *A61B 18/1477* (2013.01); *A61B 2018/1495* (2013.01)

(58) Field of Classification Search
CPC ...... A61B 2017/00278; A61B 18/1482; A61B 2018/1495; A61B 2018/00601; A61B 18/1206; A61B 2217/005; A61B 2218/007; A61B 2018/00517; A61B 17/3476
See application file for complete search history.

(56) References Cited

U.S. PATENT DOCUMENTS

| | | | |
|---|---|---|---|
| 6,623,437 | B2 | 9/2003 | Hinchliffe |
| 6,623,480 | B1 | 9/2003 | Kuo et al. |
| 6,770,070 | B1 | 8/2004 | Balbierz |
| 8,361,061 | B2 | 1/2013 | Esch et al. |
| 2006/0074471 | A1 | 4/2006 | Palm |
| 2008/0188917 | A1 | 8/2008 | Gerber et al. |
| 2010/0179630 | A1 | 7/2010 | Williams |
| 2010/0228202 | A1 | 9/2010 | O'Dea |
| 2010/0292744 | A1 | 11/2010 | Hill et al. |
| 2011/0022144 | A1 | 1/2011 | Jarl et al. |
| 2011/0087299 | A1 | 4/2011 | Ameri |
| 2012/0029652 | A1* | 2/2012 | Wagh .................. A61B 17/3478 623/23.7 |
| 2013/0090654 | A1* | 4/2013 | Clancy ............... A61B 18/1477 606/45 |
| 2013/0310833 | A1* | 11/2013 | Brown ........... A61B 17/320016 606/45 |
| 2015/0038963 | A1 | 2/2015 | Panos et al. |

FOREIGN PATENT DOCUMENTS

| | | |
|---|---|---|
| JP | 2015-512704 | 4/2015 |
| WO | WO 95/10327 | 4/1995 |
| WO | WO 96/36282 A2 | 11/1996 |
| WO | WO 99/56812 | 11/1999 |
| WO | WO-03020136 A1 | 3/2003 |

OTHER PUBLICATIONS

Japanese Office Action and translation for Japanese Application No. 2019-503413 dated Dec. 24, 2019 (9 pages).

* cited by examiner

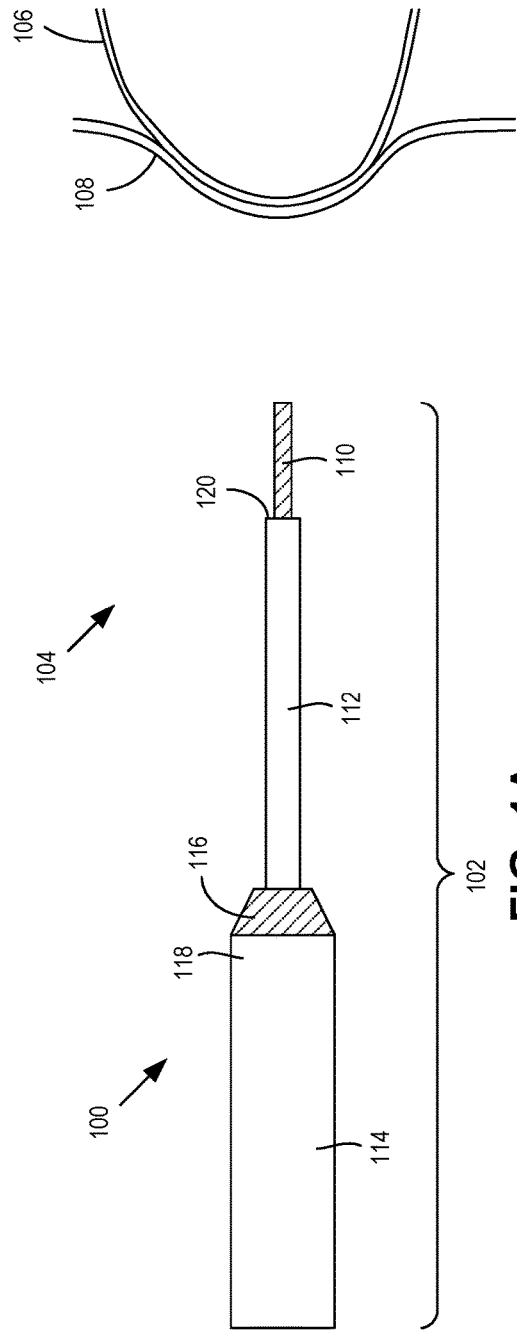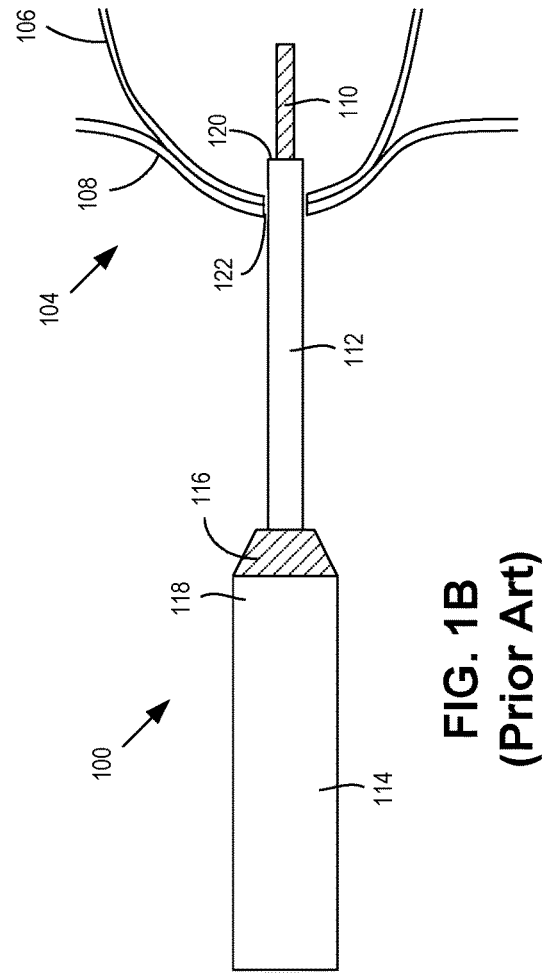

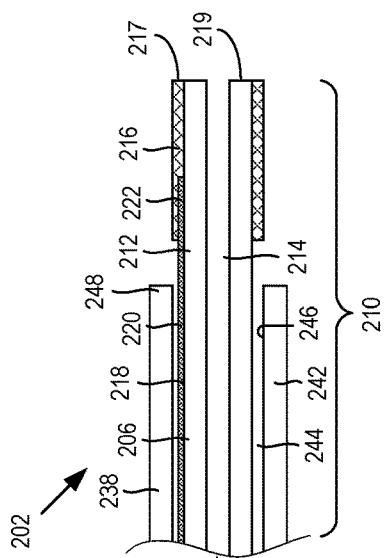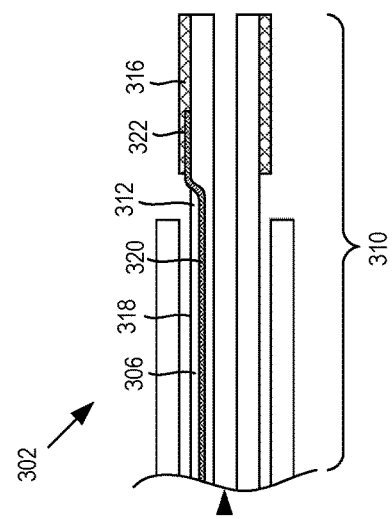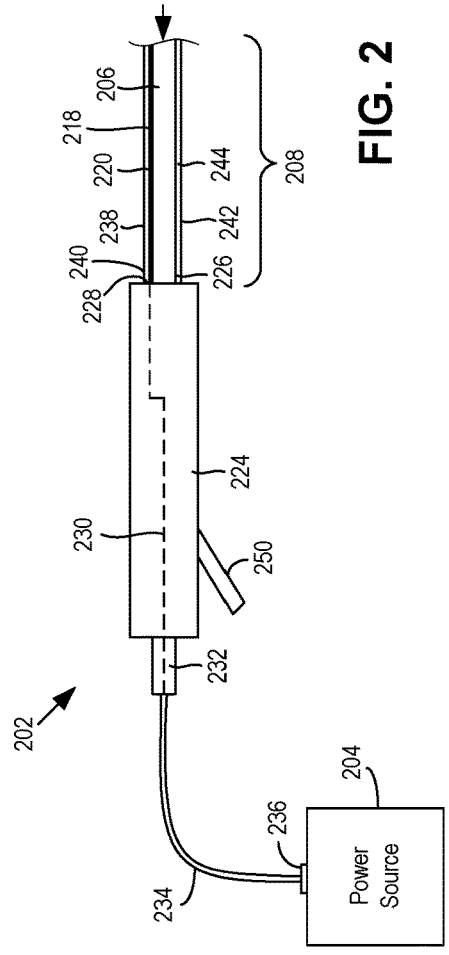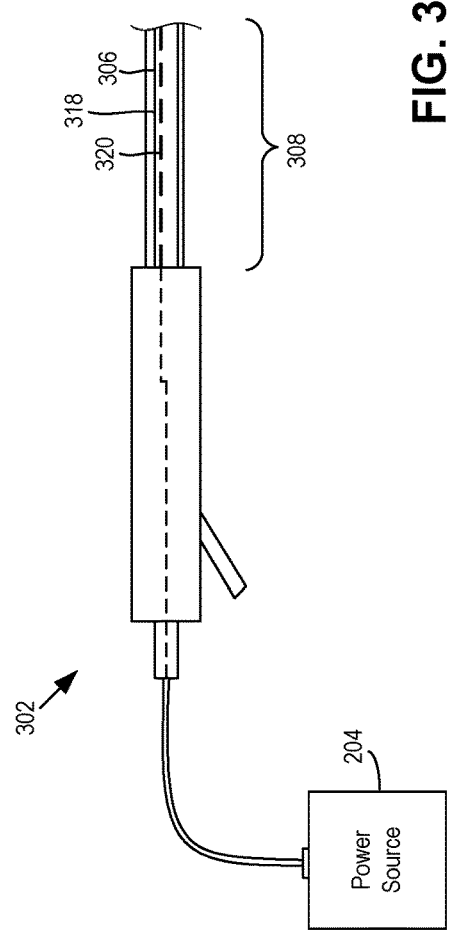
FIG. 2
FIG. 3

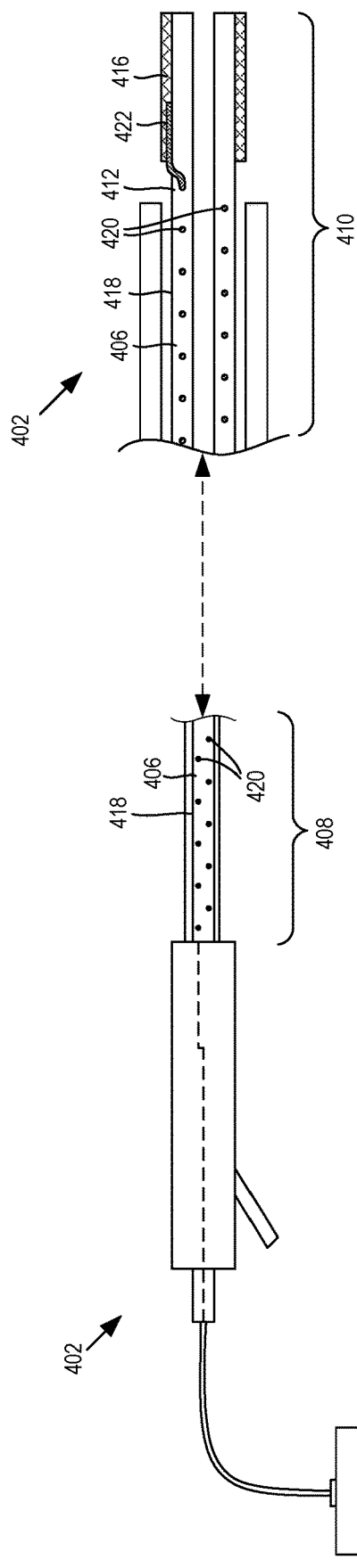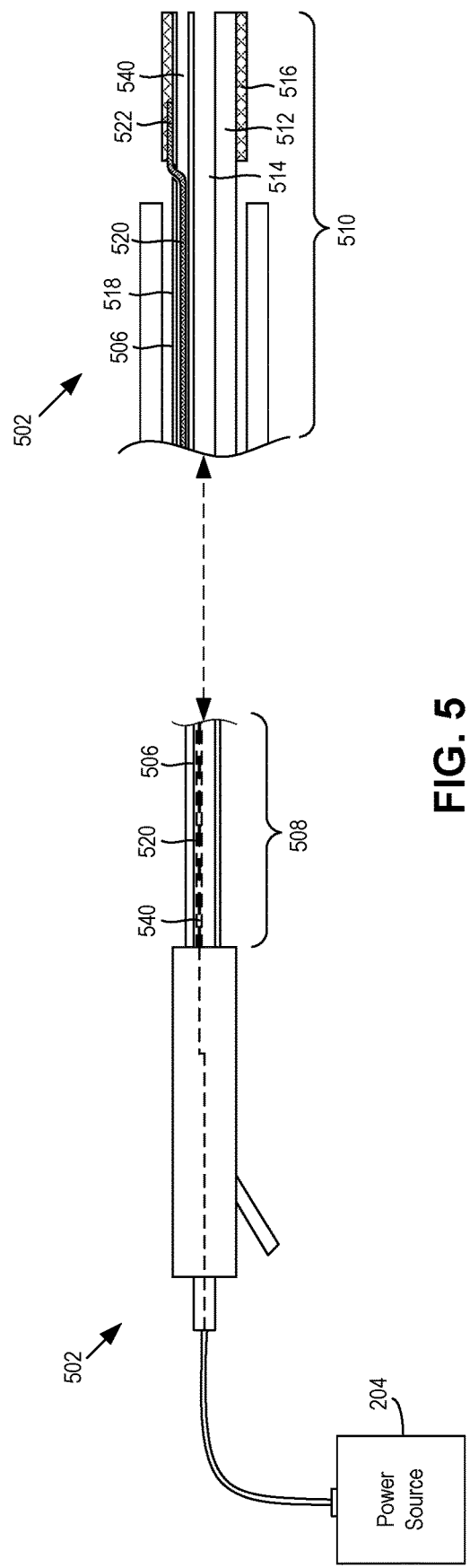

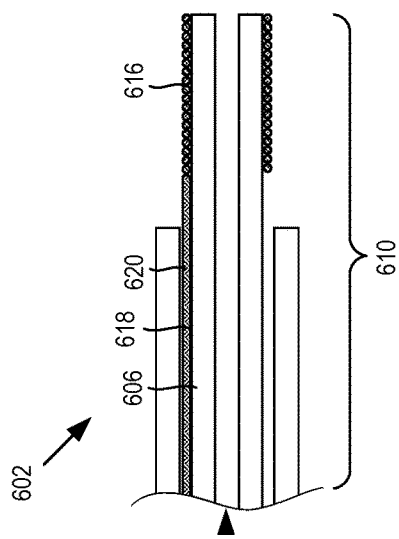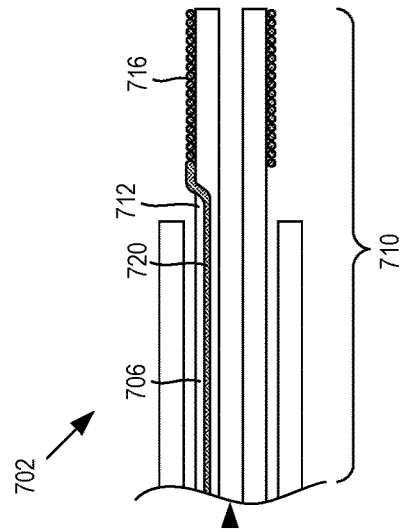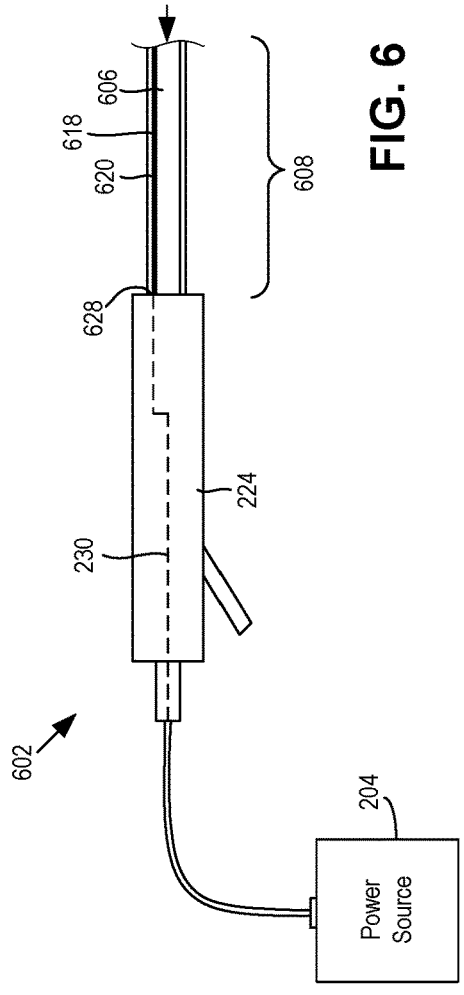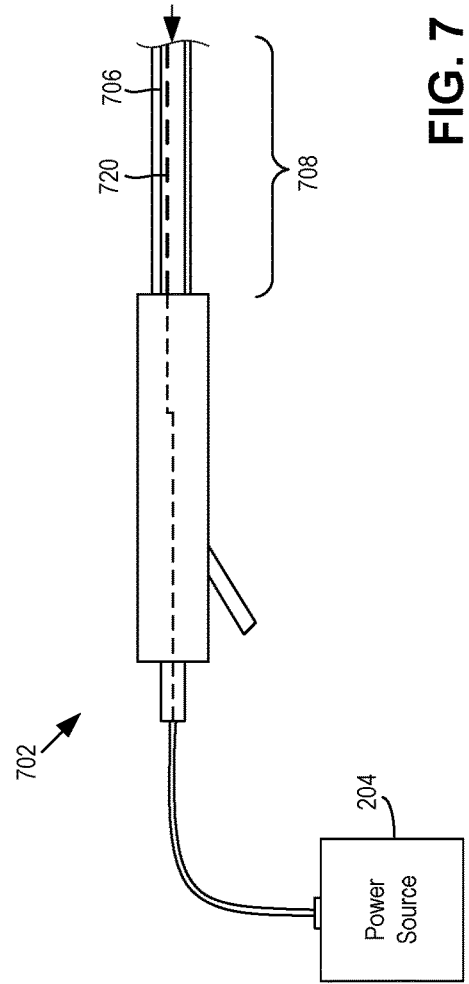
FIG. 6
FIG. 7

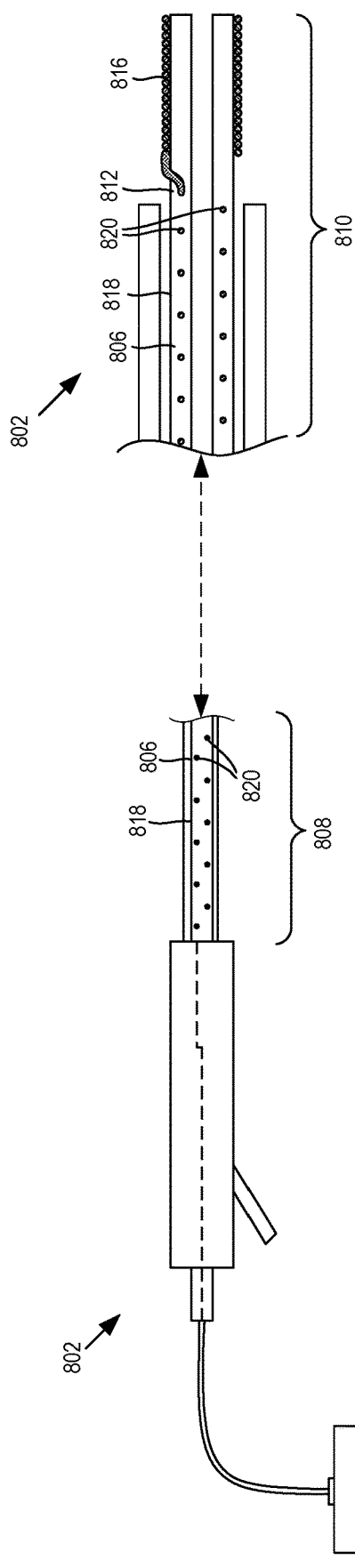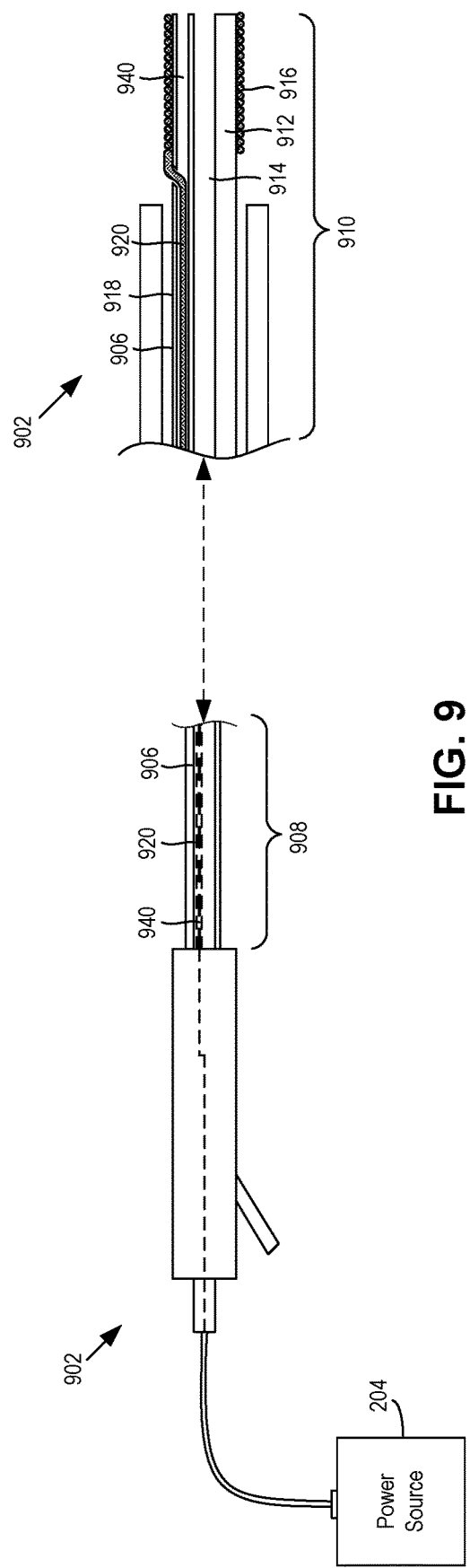
FIG. 8
FIG. 9

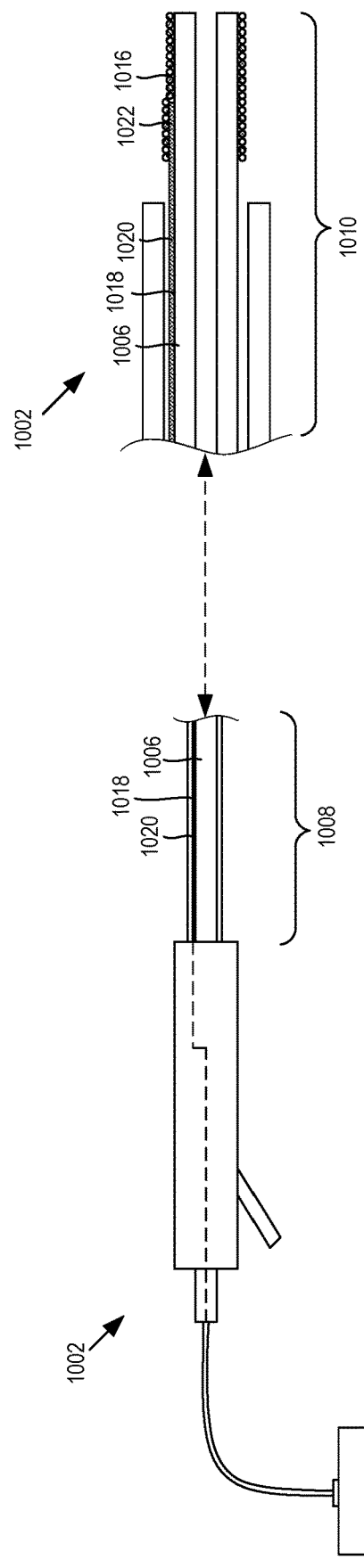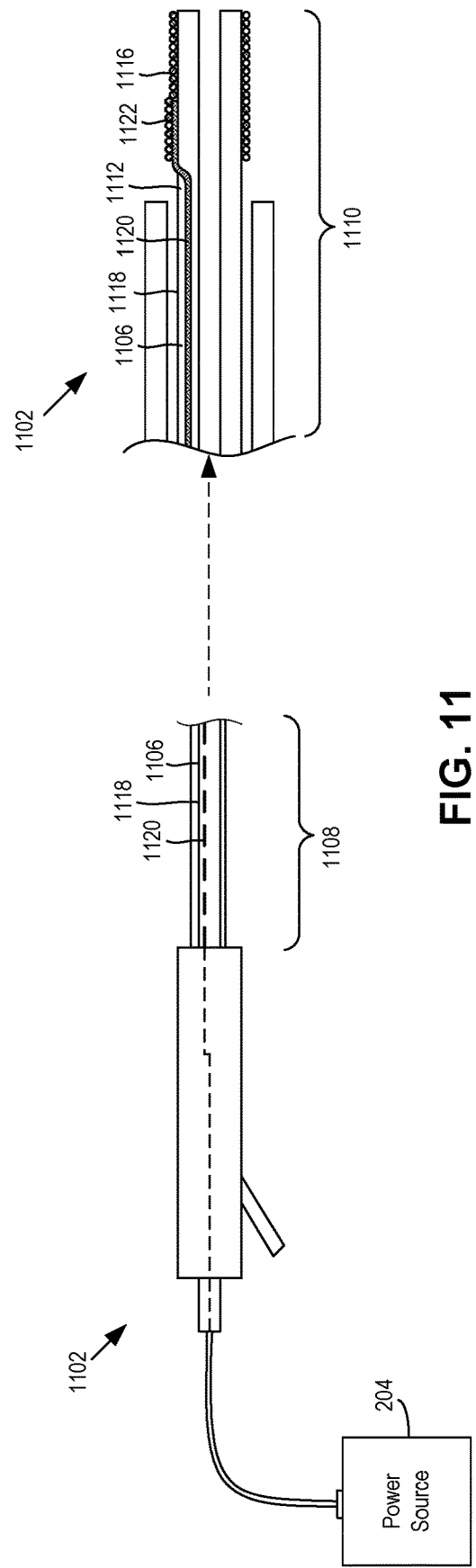

ELECTROSURGICAL DEVICES WITH A SINGLE CONDUCTIVE TUBULAR ELEMENT FOR ACCESSING ANATOMICAL STRUCTURES

This application is a Divisional of co-pending U.S. Non-Provisional application Ser. No. 15/661,670, filed Jul. 27, 2017, which claims the benefit of U.S. Provisional Application No. 62/368,639, filed Jul. 29, 2016. The contents of U.S. Non-Provisional application Ser. No. 15/661,670 and U.S. Provisional Application No. 62/368,639 are incorporated by reference in their entirety.

TECHNICAL FIELD

The present invention relates generally to medical devices, and more particularly to electrosurgical devices, systems, and related methods for using a tubular conductive element to electrosurgically create an opening for gaining access into an anatomical structure of a patient.

BACKGROUND

A cystotome is an electrosurgical medical device that cuts tissue through application of electrical current in order to gain access into for example a pancreatic pseudocyst. Once the tissue is cut and access into the pseudocyst is obtained, a subsequent procedure may be performed on the pseudocyst, such as insertion of a stent into and/or draining of fluid from the pseudocyst. FIGS. 1A-1D show a side view of a distal portion 102 of an example cystotome 100 cutting tissue at a treatment site 104 within a patient to gain access into a pseudocyst 106. An example type of pseudocyst 106 may be a pancreatic pseudocyst that pushes up against a wall 108 of the stomach or duodenum (e.g., a transgastric wall or a transduodenal wall) or of another area of the gastrointestinal (GI) tract, causing a bulge in the wall 108.

The cystotome 100 may include three elongate coaxial components: a conductive needle knife 110, an inner catheter 112 disposed over the needle knife 110, and an outer catheter 114 disposed over the inner catheter 112. A ring-shaped conductive member 116 may be attached to a distal end 118 of the outer catheter 114. The conductive member 116 may be referred to as a conductive distal tip 116 of the outer catheter 114. The inner catheter 112 may function to electrically insulate the needle knife 110 from the conductive distal tip 116. In a particular embodiment of the cystotome 100, the needle knife 110 may have a diameter of 0.038 inches (0.9652 millimeters), the inner catheter 112 may have an outer diameter of 5 French (Fr) (1.667 millimeters), and the outer catheter 114 may have an outer diameter of 10 French (3.333 millimeters). A maximum diameter of the conductive distal tip 116 may also be or relatively close to 10 French.

Although not shown in FIGS. 1A-1D, each of the needle knife 110, the inner catheter 112, and the outer catheter 114 may be operatively coupled to a handle assembly at a proximal portion. Through operation of the handle assembly, the needle knife 110, the inner catheter 112, and the outer catheter 114 may be configured to longitudinally move relative to each other, or may be locked in fixed positions relative to each other. In addition, although not shown in FIGS. 1A-1D, the needle knife 110 and the distal tip 116 may be alternatingly connected to and electrically activated by a power source via the handle assembly.

Referring to FIG. 1A, the distal portion 102 of the cystotome 100 may be delivered to the treatment site 104. As shown in FIG. 1A, a distal portion of the needle knife 110 may be moved distally past a distal end 120 of the inner catheter 112 in order to be exposed to the outer surroundings and contact the tissue it is intended to cut. In addition, the distal tip 116 may be longitudinally positioned a distance proximally away from the distal end 120 of the inner catheter 112 so that is a sufficient distance away the exposed distal portion of the needle knife 110 to avoid any electrical shorting.

Referring to FIG. 1B, the power source connected to the needle knife 110 may be activated, causing electrical current to flow through the needle knife 110. The distal portion 102 may be distally advanced so that the distal portion of the electrically activated needle knife 110 contacts and cuts into the bulging part of the wall 108. The distal portion 102 may continue to be distally advanced so that the needle knife 110 cuts into the wall 108 and then into the pseudocyst 106 to make an incision 122. As shown in FIG. 1B, at this point during the procedure, distal portions of the needle knife 110 and the inner catheter 112 may have gained access to and be disposed in the pseudocyst 106, while the outer catheter 114 may still be outside the pseudocyst 106.

Referring to FIG. 1C, the incision 122 made by the needle knife 110 may be too small for a subsequent procedure, such as insertion of a stent or other drainage device into the pseudocyst 106. To make the incision 122 larger, the 10 French conductive distal tip 116 may be used. In particular, the needle knife 110 may be electrically deactivated and disconnected from the power source, and proximally withdrawn away from the treatment site 104 to outside of the patient. A wire guide 124 may then be distally advanced through the inner catheter 112 until a distal portion of the wire guide 124 is disposed in the pseudocyst 106. The wire guide 124 may help to stabilize the inner catheter 112 in the pseudocyst 106 after the needle knife 110 is withdrawn. FIG. 1C shows the distal portion of wire guide 124 having curled within the pseudocyst 106. In addition, the conductive distal tip 116 may be electrically coupled to the power source via a conductive wire 126 attached to the distal tip 116. The conductive wire 126 may be attached and electrically connected to the distal tip 116 using solder 128. Additionally, the wire 126 may longitudinally extend in between an outer surface of the inner catheter 112 and an inner surface of the outer catheter 116. Although not shown, the wire 126 may proximally extend to the handle assembly outside of the patient, and the handle assembly may electrically couple the wire 126 to the power source. The outer catheter 114 may be distally advanced toward the wall 108. The distal tip 116 may be electrically activated using the power source and may perform a second cut into the wall 108 and then into the pseudocyst 106 to enlarge the incision 122. The inner catheter 112 may function as an insulator between the electrically activated distal tip 116 and the wire guide 124.

Referring to FIG. 1D, after the distal tip has sufficiently cut into the pseudocyst 106 and enlarged the incision 122, the conductive distal tip 116 may be deactivated and the inner and outer catheters 112, 114 may be proximally withdrawn from the treatment site 104 to outside the patient. The wire guide 124 may be left in place, with the distal portion of the wire guide 124 remaining in the pseudocyst 106. Thereafter, a subsequent procedure associated with the pseudocyst 106 may be performed. For example, a delivery device may be distally advanced over the wire guide 124 toward the treatment site 104 to place a stent or other drainage device in the pseudocyst 106.

In some situations, insertion of a stent or other drainage device in a range from five French to ten French may be desirable. However, the size of the incision 122 after being enlarged by the ten French conductive tip 116 may be too large for such a stent or other drainage device to be securely maintained in the pseudocyst. At the same time, the size of the incision 122 made by the needle knife 110 may be too small. Merely reducing the diameter of the conductive tip 116 to be smaller than ten French may not be feasible since the power required to cut through the wall 108 and into the pseudocyst 106 (e.g, 80-120 Watts) may cause such a reduced-size conductive tip to generate heat at a level that melts the solder attaching the conductive tip 116 to the wire 126, which in turn may cause the distal tip 116 to lose its electrical connection with the wire 126 and ultimately the power source. Additionally, having to perform two cuts with two different conductive elements (i.e., the needle knife 110 and the conductive tip 116) to form the incision 122 is time consuming and cumbersome. As such, it may be desirable for a cystotome to have a single conductive element to perform the cutting and make a sufficiently-sized incision that allows a five-to-ten French stent or other drainage device to be inserted into and securely maintained in the pseudocyst.

BRIEF SUMMARY

By way of introduction, the below embodiments relate to electrosurgical devices, systems, and methods for using a tubular conductive element to electrosurgically create an opening for gaining access into an anatomical structure of a patient. In a first embodiment, an electrosurgical device includes an elongate tubular member, a conductive tubular element, and an elongate conductive member. The elongate tubular member extends from a proximal portion to a distal portion and includes a body and a wireguide lumen longitudinally extending in the body from the proximal portion to the distal portion. The body includes an insulating material. The conductive tubular element is affixed to the body and disposed about an outer surface of the body at the distal portion. The insulating material of the body insulates the wireguide lumen from the conductive tubular element. The elongate conductive member longitudinally extends adjacent the body from the proximal portion to the distal portion. A distal portion of the elongate conductive member is attached and electrically connected to the conductive tubular element.

In some embodiments, the conductive tubular element is disposed over the distal portion of the elongate conductive member.

In some embodiments, the conductive tubular element includes a conductive cannula.

In some embodiments, the conductive tubular element includes a conductive coil.

In some embodiments, the conductive coil and the elongate conductive member are integral components of a same wire.

In some embodiments, the conductive coil and the elongate conductive member are parts of different wires.

In some embodiments, the conductive tubular element includes a conductive coil and a conductive cannula disposed over the conductive coil.

In some embodiments, the elongate conductive member longitudinally extends outside and along an outer surface of the body from the proximal portion to the distal portion.

In some embodiments, the elongate conductive member longitudinally extends inside the body from the proximal portion to the distal portion. The distal portion of elongate conductive member extends from inside to outside of the elongate tubular member to be attached to the conductive tubular member.

In some embodiments, the elongate conductive member is embedded in the body.

In some embodiments, the elongate conductive member is in a straightened configuration while embedded in the body.

In some embodiments, the elongate conductive member is in a coiled configuration while embedded in the body.

In some embodiments, the wireguide lumen includes a first lumen, and the elongate tubular member further includes a second lumen longitudinally extending in the body from the proximal portion to the distal portion. The elongate tubular member longitudinally extends in the second lumen from the proximal portion to the distal portion.

In some embodiments, an outer diameter of the conductive tubular element is greater than five French (one and two-thirds millimeters) and less than ten French (three and one-third millimeters).

In some embodiments, the outer diameter of the conductive tubular element is six French.

In another embodiment, a method of gaining access into an anatomical structure may be performed. The method may include delivering a conductive tubular element to a treatment site in a patient; electrically activating the conductive tubular element; and creating an opening in the anatomical structure by initially cutting the anatomical structure with the electrically activated conductive tubular element.

In some embodiments, creating the opening includes creating an incision in the anatomical structure.

In some embodiments, creating the opening includes enlarging an initial opening of the anatomical structure.

In some embodiments, creating the opening includes creating the opening with only the electrically activated conductive tubular element.

In some embodiments, initially cutting into the anatomical structure comprises distally advancing a distal end of the conductive tubular element into the anatomical structure while the conductive tubular element is electrically activated.

In some embodiments, initially cutting into the anatomical structure includes initially cutting into the anatomical structure with a side surface defining a distal end of the conductive tubular element.

In some embodiments, the method further includes: after creating the opening, positioning a drainage device in the opening for drainage of the anatomical structure.

In some embodiments, the method further includes: before positioning the drainage device in the opening, distally advancing a distal portion of a wireguide through the opening to within the anatomical structure; and distally advancing the drainage device over the wireguide to the treatment site in order to position the drain device in the opening.

In some embodiments, the conductive tubular element is disposed about an elongate tubular member, distally advancing the distal portion of the wireguide comprises distally advancing the distal portion through a wireguide lumen of the elongate tubular member.

In some embodiments, an outer diameter of the conductive tubular element is greater than five French (one and two-thirds millimeters) and less than ten French (three and one-third millimeters).

In some embodiments, the conductive tubular element includes at least one of a conductive cannula or a conductive coil.

In some embodiments, the method further includes: delivering electrical current in a range of 80-120 Watts to the conductive tubular element while the conductive tubular element is cutting into the anatomical structure to create the opening.

In some embodiments, delivering the conductive tubular element to the treatment site comprises delivering the conductive tubular element disposed over an elongate tubular member comprising a body and a wireguide lumen longitudinally extending through the body, where the body includes an insulating material that electrically insulates the wireguide lumen from the conductive tubular element.

In some embodiments, the treatment site is in a gastrointestinal tract of the patient.

In some embodiments, the anatomical structure is adjacent a wall of the gastrointestinal tract, and the method further includes cutting into the wall before cutting into the anatomical structure in order to create the opening.

In some embodiments, the anatomical structure includes a pseudocyst.

In some embodiments, the pseudocyst is adjacent a wall outside the gastrointestinal tract.

Other embodiments are possible, and each of the embodiments can be used alone or together in combination. Accordingly, various embodiments are described below with reference to the attached drawings.

BRIEF DESCRIPTION OF THE DRAWINGS

FIG. 1A is a side view of a distal portion of a prior art cystotome delivered to a treatment site near a pseudocyst.

FIG. 1B is a side view of the distal portion of the prior art cystotome of FIG. 1A, with a needle knife disposed in an inner elongate tubular member having cut into the pseudocyst.

FIG. 2 is a partial cross-sectional side view of a first example electrosurgical device configured to gain access into a pseudocyst that includes a conductive cannula and an elongate conductive member longitudinally extending on an outer surface of an elongate tubular member.

FIG. 3 is a partial cross-sectional side view of a second example electrosurgical device configured to gain access into a pseudocyst that includes a conductive cannula and an elongate conductive member longitudinally extending while embedded in a body of an elongate tubular member in a generally straightened manner.

FIG. 4 is a partial cross-sectional side view of a third example electrosurgical device configured to gain access into a pseudocyst that includes a conductive cannula and an elongate conductive member embedded in a body of an elongate tubular member in a coiled configuration.

FIG. 5 is a partial cross-sectional side view of a fourth example electrosurgical device configured to gain access into a pseudocyst that includes a conductive cannula and an elongate conductive member longitudinally extending in a lumen of the elongate tubular member.

FIG. 6 is a partial cross-sectional side view of a fifth example electrosurgical device configured to gain access into a pseudocyst that includes a conductive coil integral with an elongate tubular member longitudinally extending on an outer surface of an elongate tubular member.

FIG. 7 is a partial cross-sectional side view of a sixth example electrosurgical device configured to gain access into a pseudocyst that includes a conductive coil integral with an elongate tubular member that longitudinally extends in a generally straightened manner while embedded in a body of an elongate tubular member.

FIG. 8 is a partial cross-sectional side view of a seventh example electrosurgical device configured to gain access into a pseudocyst that includes a first conductive coil integral with a second conductive coil embedded in a body of an elongate tubular member.

FIG. 9 is a partial cross-sectional side view of an eight example electrosurgical device configured to gain access into a pseudocyst that includes a conductive coil integral with an elongate conductive member longitudinally extending in a lumen of an elongate tubular member.

FIG. 10 is a partial cross-sectional side view of a ninth example electrosurgical device configured to gain access into a pseudocyst that includes a conductive coil disposed over a distal end of a separate elongate conductive member longitudinally extending on an outer surface of an elongate tubular member.

FIG. 11 is a partial cross-sectional side view of a tenth example electrosurgical device configured to gain access into a pseudocyst that includes a conductive coil disposed over a distal end of a separate elongate conductive member longitudinally extending in a generally straightened manner while embedded in a body of an elongate tubular member.

DETAILED DESCRIPTION

Figure 1C:
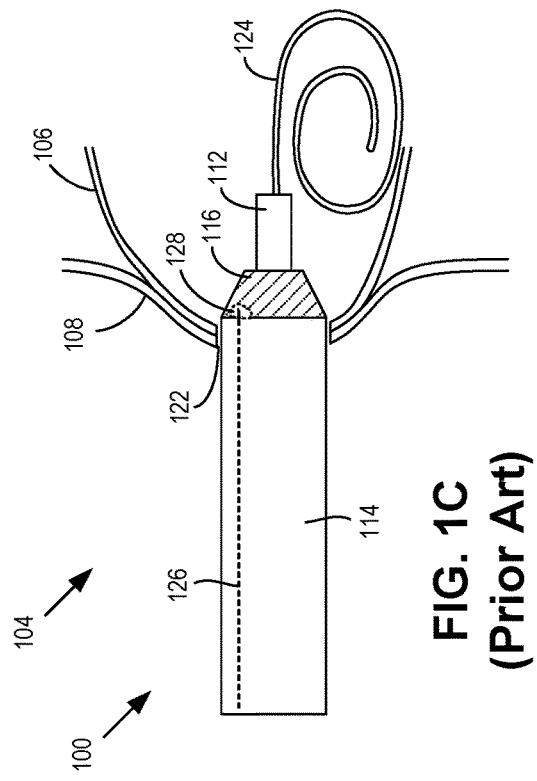
FIG. 1C is a side view of the distal portion of the prior art cystotome of FIG. 1A, with a conductive cannula coupled to an outer elongate tubular member having further cut into the pseudocyst and a distal portion of a wireguide being inserted into the cystotome.
Figure 1D:
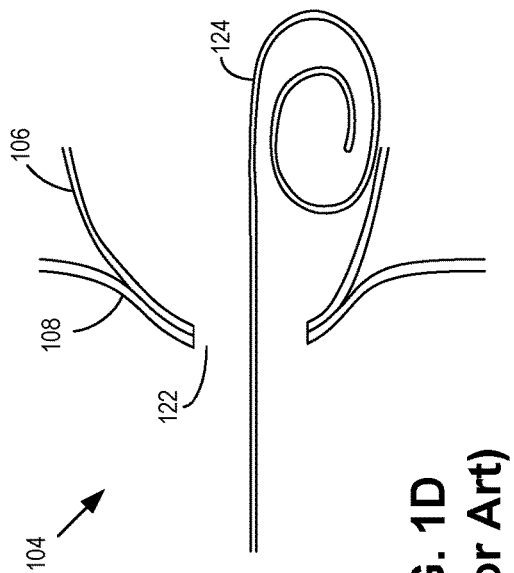
FIG. 1D is a side view of the distal portion of the wireguide being left in the pseudocyst with the distal portion prior art cystotome of FIG. 1A having been removed from the treatment site.

The present disclosure describes various exemplary embodiments of an electrosurgical device that includes a conductive distal tip that is configured to create an opening in order to gain access into an anatomical structure, such as one that is in or adjacent to the gastrointestinal tract of a patient. The present disclosure also describes related methods of gaining access into anatomical structure using the various exemplary embodiments of the electrosurgical device.

The conductive distal tip may include a conductive tubular or cylindrical element disposed about an outer surface of an elongate tubular member, such as a catheter, at a distal portion of the elongate tubular member. The cylindrical conductive distal tip may be made of a conductive material, such as stainless steel or copper as non-limiting examples. Other conductive materials may be possible. In some example embodiments, the conductive tubular element may be a cannula that is a continuous, solid structure and/or that has a generally smooth outer surface over its longitudinal length. In other example embodiments, the conductive tubular element may be a coil or coiled structure, such as a coiled wire, that is a discontinuous structure over its longitudinal length and/or that has a generally ribbed outer surface over its longitudinal length as formed by the coils. In still other example embodiments, the conductive tubular element may be combination of the cannula and the coil. A longitudinal length of the conductive tubular element may be in a range from three to eight millimeters, although other longitudinal lengths may be possible.

In addition to being disposed about the elongate tubular member, the conductive distal tip may also be affixed to the elongate tubular member. By being affixed to the elongate tubular member, the distal tip may longitudinally move with the elongate tubular member. In other words, the elongate tubular member may be longitudinally moved in order to longitudinally move the conductive distal tip.

The tubular conductive distal tip may have an outer diameter, and/or the tubular conductive distal tip in combination with the elongate tubular member, may have a total outer diameter that is greater than five French (1.67 millimeters) and less than 10 French (3.33 millimeters). In one example, the total outer diameter is 6 French. In some example embodiments, the elongate tubular member itself may have an outer diameter of five French, and the total outer diameter of the conductive distal tip and the elongate tubular member may be five French plus the thickness of the conductive distal tip. An example thickness of the conductive distal tip may be four one-thousandths of an inch (0.1016 millimeters), although other thicknesses may be possible. With an outer diameter in between five French and ten French, the tubular conductive distal tip may be suitably sized to make an optimally sized incision into a pseudocyst for insertion of a stent or other drainage device having a size or outer diameter of less than ten French, without the need to additionally use other-sized conductive elements to assist in making the incision.

The conductive distal tip may be attached and electrically connected to an elongate conductive member, such as a wire, that longitudinally extends with the elongate tubular member from a proximal portion to the distal portion. Like the conductive distal tip, the elongate conductive member may be made of a conductive material, such as stainless steel or copper as non-limiting examples. The conductive distal tip may be fixedly attached to the elongate conductive member through one or more attachment mechanism other than solder. The attachment mechanism(s) used may depend on the configuration of the conductive distal tip. Where the conductive distal tip includes a cannula, the cannula may be crimped to the elongate conductive member, welded to the elongate conductive member, or a combination thereof. Where the conductive distal tip includes a coil, the coil and the elongate conductive member may be part of and/or formed from different wires, in which case the coil may be crimped and/or welded to the elongate conductive member, similar to how the cannula is attached to the elongate conductive member. Alternatively, the coil and the elongate conductive member may be part of and/or formed from the same wire, in which case the coil and the elongate conductive member are attached to each other by virtue of being part of and/or formed from the same wire.

The elongate conductive member may longitudinally extend with and/or adjacent to the body of the elongate tubular member in various ways. In some example embodiments, the elongate conductive member may extend along the outer surface and/or outside of the elongate tubular member. In other example embodiments, the elongate conductive member may longitudinally extend within the elongate tubular member. When extending within the elongate tubular member, a distal portion of the elongate conductive member may extend to outside of the elongate tubular member, where it may be attached and electrically connected to the conductive distal tip. Additionally, for some embodiments where the elongate conductive member extends within the elongate tubular member, the elongate conductive member may be embedded in a body of the elongate tubular member. For other embodiments, the elongate conductive member may be disposed and longitudinally extend in a lumen of the elongate tubular member. Where the elongate conductive member is embedded in the body, the conductive member may longitudinally extend in the body in a generally straightened configuration or in a coiled configuration.

FIGS. 2-14 show various example embodiments of an electrosurgical device that includes a conductive tubular distal tip attached and electrically connected to an elongate conductive member in accordance with the description provided above. The electrosurgical device may be part of an electrosurgical medical system along with a power source configured to supply electrical current to the distal tip.

Referring to FIG. 2, a partial cross-sectional side view of a first example embodiment of an electrosurgical device 202 in electrical connection with a power source 204 is shown. The power source 204 may be an electronic device, such as a radio frequency (RF) generator or an electrosurgical unit (ESU) that is configured to generate and supply electrical current, including RF electrical current, to the electrosurgical device 202.

The electrosurgical device 202 may include an elongate tubular member 206, such as a catheter, that longitudinally extends from a proximal portion 208 to a distal portion 210. The elongate tubular member 206 may include a body 212 and a wireguide lumen 214 longitudinally extending in the body 212 from the proximal portion 208 to the distal portion 210. The wireguide lumen 214 may be sized to have a wireguide movably disposed therein. An example size (i.e., diameter) of the wireguide lumen 214 may be in a range of about 0.010 inches to 0.040 inches. Particular example sizes may include 0.035 inches or 0.038 inches. The body 212 may be made of an insulating material such as polyether ether ketone (PEEK) or polytetrafluoroethylene (PTFE) as examples, although other insulating materials may be possible.

The electrosurgical device 202 may further include a conductive cannula 216 disposed on or about an outer surface 218 of the elongate tubular member 206 at the distal portion 210. In one example embodiment, as shown in FIG. 2, a distal end 217 of the conductive cannula 216 may be flush or even with a distal end 219 of the elongate tubular member 206. This way, when the distal portion is delivered to a treatment site, a side surface of cannula 216 defining the distal end 217 may come into contact with an anatomical structure, so that when activated by electrical energy, the side surface is able to cut the tissue of the anatomical structure, as described in further detail below. In other example embodiments, the distal end 217 of the cannula 216 may extend distally past the distal end 219 of the elongate tubular member 206. The insulating material of the body 212 of the tubular member 206 may insulate the wireguide lumen 214 (or a wireguide inside the wireguide lumen) from the conductive cannula 216.

The conductive cannula 216 may be configured to be electrically activated by the power source 204 via an elongate conductive member 220, such as a wire. The elongate conductive member 220 may longitudinally extend along or adjacent to the outer surface 218 from the proximal portion 208 to the distal portion 210. At the distal portion 210, a distal end 222 of the elongate conductive member 220 may be fixedly attached and electrically connected to the conductive cannula 216. As shown in FIG. 2, the distal end 222 may lay or otherwise be disposed on the outer surface 218, and the conductive cannula 216 may be disposed over and/or cover the distal end 222. The conductive cannula 216 may be then fixedly attached to the distal end 222 by performing a mechanical process (e.g., a crimping process that crimps the conductive cannula 216 to the distal end 222) and/or a thermal process (e.g., a welding process that welds the conductive cannula 216 to the distal end 222). The conductive cannula 216 may be fixedly attached to the distal end 222 without the use of solder, although in some configurations, solder may be added to enhance the fixed attachment.

The electrosurgical device 202 may further include a handle assembly 224 operatively coupled to proximal ends 226, 228 of the elongate tubular member 206 and the elongate conductive member 220. The elongate conductive member 220 may be electrically coupled to the power source 204 via the handle assembly 224. For example, as shown in FIG. 2, the handle assembly 224 may include a conductive coupling element 230 configured to be electrically coupled to the proximal end 228 of the elongate conductive member 220. The handle assembly 224 may also include a connector 232 adapted to be connected to electrical cabling 234, which may also be connected to an output port 236 of the power source 204. For some example configurations, the electrical cabling 234 may be adapted to be removably connected to the handle connector 232 and/or the output port 236. When the electrical cabling 234 is connected to the output port 236 of the power source 204 and the connector 232 of the handle assembly 224, the power source 204 may be configured to deliver electrical current to the elongate conductive member 220 via the electrical cabling 234 and the conductive coupling element 234 of the handle assembly 224. In turn, the elongate conductive member 220 may deliver the electrical current to the conductive cannula 216. In addition, as shown in FIG. 2, the handle assembly 224 may include a wireguide portion 250 in communication with the wireguide lumen 214 for insertion of a wireguide into the wireguide lumen 214 and removal therefrom.

For some example configurations, the elongate tubular member 206 may be an inner elongate tubular member 206, and the electrosurgical device 202 may further include an outer elongate tubular member 238 coaxial with the inner elongate tubular member 206. The outer elongate tubular member 238 may longitudinally extend from the proximal portion 208 to the distal portion 210, and a proximal end 240 may be coupled to the handle assembly 224. The outer elongate tubular member 238 may include a body 242 and a central lumen 244 longitudinally extending in the body 242. The inner elongate tubular member 206 may longitudinally extend within the central lumen 244 from the proximal portion 208 to the distal portion 210. The elongate conductive member 220 may longitudinally extend in between the outer surface 218 of the inner elongate tubular member 206 and an inner surface 246 of the body 240 of the outer elongate tubular member 238 defining the central lumen 242.

The handle assembly 224 may be configured to longitudinally move the inner elongate tubular member 206, the conductive cannula 216, and the elongate conductive member 220 relative to the outer elongate tubular member 238. During operation, when the distal portion 206 is being delivered to a treatment site within a patient, the handle assembly 224 may move the inner and outer elongate tubular members 206, 238 relative to each other so that the conductive cannula 216 is disposed inside the outer member 238, such as within the central lumen 244. Subsequently, at the treatment site, the handle assembly 224 may move the inner and outer elongate tubular members 206, 238 relative to each other so that the conductive cannula 216 is distally past a distal end 248 of the outer member 238 and exposed to its outer surroundings so that the conductive cannula 216 may contact tissue to perform the electrosurgical procedure. For other example configurations, the electrosurgical device 202 may not include the outer elongate tubular member 238.

Referring to FIG. 3, a partial cross-sectional side view of a second example embodiment of an electrosurgical device 302 in electrical connection with the power source 204 is shown. The electrosurgical device 302 of FIG. 3 may be similar to the electrosurgical device 202 of FIG. 2, except that, as shown in FIG. 3, the electrosurgical device 302 may include an elongate conductive member 320 that is embedded in a body 312 of an elongate tubular member 306. While embedded in the body 312, the elongate conductive member 320 may longitudinally extend from a proximal portion 308 to a distal portion 310 in a generally straightened manner. At the distal portion 310, the elongate conductive member 320 may extend to outside the elongate tubular member 306, and a distal portion 322 may lay or otherwise be disposed on an outer surface 318 of the elongate tubular member 306. Like the electrosurgical device 202 of FIG. 2, a conductive cannula 316 may disposed about the outer surface 318 of the elongate tubular member 306 and over the distal end 322 of the elongate conductive member 306. The conductive cannula 316 may be fixedly attached to the distal end 322, such as by use of a mechanical (e.g., crimping) and/or a thermal (e.g., welding) process.

Referring to FIG. 4, a partial cross-sectional side view of a third example embodiment of an electrosurgical device 402 in electrical connection with the power source 204 is shown. The third embodiment 402 is similar to the second and third embodiments 202, 302, except that, as shown in FIG. 4, the electrosurgical device 402 may include an elongate conductive member 420 that is in a coiled configured while embedded and longitudinally extending in a body 412 of an elongate tubular member 406 from a proximal portion 408 to a distal portion 410. A distal portion 422 of the embedded coil 420 may extend from the body 412 to an outer surface 418 of the elongate tubular member 406, where a conductive cannula 416 may be disposed over and fixedly attached to the distal portion 422. FIG. 4 shows the distal portion 422 in a generally straightened configuration when disposed outside the elongate tubular member 406, although in other configurations, the distal portion 422 may maintain the coiled configuration when disposed outside and on the outer surface 418.

Referring to FIG. 5, a partial cross-sectional side view of a fourth example embodiment of an electrosurgical device 502 in electrical connection with the power source 204 is shown. The fifth example embodiment 502 may be similar to the second example embodiment 302 of FIG. 3, except instead of being embedded in the body, the fourth example embodiment may include a lumen in which the elongate conductive member may be disposed. In particular, the fifth example embodiment of the electrosurgical device 502 may include two lumens longitudinally extending in a body 512 of an elongate tubular member 506 from a proximal portion 508 to a distal portion 510. The two lumens may include a wireguide lumen 514 and a second lumen 540 for an elongate conductive member 520. The elongate conductive member 520 may longitudinally extend in the second lumen 540 from the proximal portion 508 to the distal portion 510. At the distal portion 510, a distal portion 522 of the elongate conductive member 520 may exit the second lumen 540 and distally extend to outside the elongate tubular member 506, where the distal portion 522 may be disposed on an outer surface 518 of the elongate tubular member 506. Like the first through third example embodiments, a conductive cannula 516 may be disposed over and fixedly attached to the distal portion 522.

Referring to FIG. 6, a partial cross-sectional side view of a fifth example embodiment of an electrosurgical device 602 in electrical connection with the power source 204 is shown. Rather than include a conductive cannula as in the first through fourth example embodiments of FIGS. 2-5, the fifth example embodiment of the electrosurgical device 602 may include a conductive coil 616 disposed on or about an outer surface 618 of an elongate tubular member 606 at a distal portion 610. Like the first example embodiment 202 of FIG. 2, the electrosurgical device 602 may also include an elongate conductive member 620 that longitudinally extends along the outer surface 618 from a proximal portion 608 to the distal portion 610. A proximal end 628 of the elongate conductive member 620 may be electrically coupled to the coupling element 230 of the handle assembly 224 in order to electrically couple the conductive coil 616 with the power source 204. In the fifth example embodiment 602 of FIG. 6, the conductive coil 616 and the elongate conductive member 620 may be integral components of the same wire. Also, FIG. 6 shows the elongate conductive member 620 extending from the proximal portion 608 to the distal portion 610 in a generally straightened configuration. In other example configurations, the elongate conductive member 620 may have coiled configuration as it extends from the proximal portion 608 to the distal portion 610.

Referring to FIG. 7, a partial cross-sectional side view of a sixth example embodiment of an electrosurgical device 702 in electrical connection with the power source 204 is shown. The sixth example embodiment 702 may be similar to the fifth example embodiment 602 of FIG. 6, except that the electrosurgical device 702 may include an elongate conductive member 720 embedded in a body 712 of an elongate tubular member 706 while longitudinally extending in the body 712 from a proximal portion 708 to a distal portion 710. As shown in FIG. 7, the elongate conductive member 720 may longitudinally extend in the body 712 in a generally straightened manner. In addition, like the fifth example embodiment 602 of FIG. 6, the elongate conductive member 720 and a conductive coil 716 may be integral components of the same wire.

Referring to FIG. 8, a partial cross-sectional side view of a seventh example embodiment of an electrosurgical device 802 in electrical connection with the power source 204 is shown. The electrosurgical device 802 may include a first conductive coil 816 disposed on an outer surface 818 of an elongate tubular member 806 at a distal portion 810. The electrosurgical device 802 may also include a second conductive coil 820 embedded in a body 812 of the elongate tubular member 806. The second conductive coil 820 may extend from a proximal portion 808 to the distal portion 810. In the example embodiment 802, the first conductive coil 816 and the second conductive coil 820 may be integral components of the same wire. At the distal portion 810, the wire may extend from the body 812 to outside the elongate tubular member 806, where the wire forms the first conductive coil disposed on the outer surface 818.

Referring to FIG. 9, a partial cross-sectional side view of an eighth example embodiment of an electrosurgical device 902 in electrical connection with the power source 204 is shown. The eighth example embodiment 902 may include a wireguide lumen 914 and a second lumen 940 longitudinally extending in a body 912 from a proximal portion 908 to a distal portion 910 of an elongate tubular member 906. An elongate conductive member 920 may be disposed and longitudinally extend within the second lumen 920 from the proximal portion 908 to the distal portion 910. Similar to the fifth, sixth, and seventh example embodiments 602, 702, 802 of FIGS. 6-8, the elongate conductive member 920 and a conductive coil 916 may be integral components of the same wire. At the distal portion 910, the elongate conductive member 920 may exit the second lumen 940 and extend to outside the elongate tubular member 906 to form the conductive coil 916 disposed on an outer surface 918 of the elongate tubular member 906.

FIGS. 10-13 are partial cross-sectional side views of ninth, tenth, eleventh, and twelfth example embodiments of electrosurgical devices 1002, 1102, 1202, 1303, respectively. These example embodiments are similar to the first, second, third, and fourth example embodiments 202, 302, 402, 502, respectively, except that they each include a conductive coil as the conductive distal tip instead of a conductive cannula. In each of the embodiments, though, the conductive coil and a respective elongate conductive member may parts of different wires. Accordingly, the conductive coils may be attached to their respective elongate conductive members through a mechanical process (e.g., crimping) and/or a thermal process (e.g., welding).

In further detail, referring to FIG. 10, an elongate conductive member 1020 may longitudinally extend along an outer surface 1018 of an elongate tubular member 1006 from a proximal portion 1008 to a distal portion 1010. At the distal portion 1010, a conductive coil 1016 may cover and be fixedly attached and electrically connected to a distal portion 1022 of the elongate conductive member 1020.

Referring to FIG. 11, an elongate conductive member 1120 may be embedded and longitudinally extend in a body 1112 of an elongate tubular member 1106 from a proximal portion 1108 to a distal portion 1110. At the distal portion 1110, a distal portion 1122 of the elongate conductive member 1120 may extend from the body 1112 to outside the elongate tubular member 1106, where the distal portion 1122 is disposed on an outer surface 1118. A conductive coil 1116 may cover and be fixedly attached and electrically connected to the distal portion 1122 of the elongate conductive member 1120.

Figure 12:
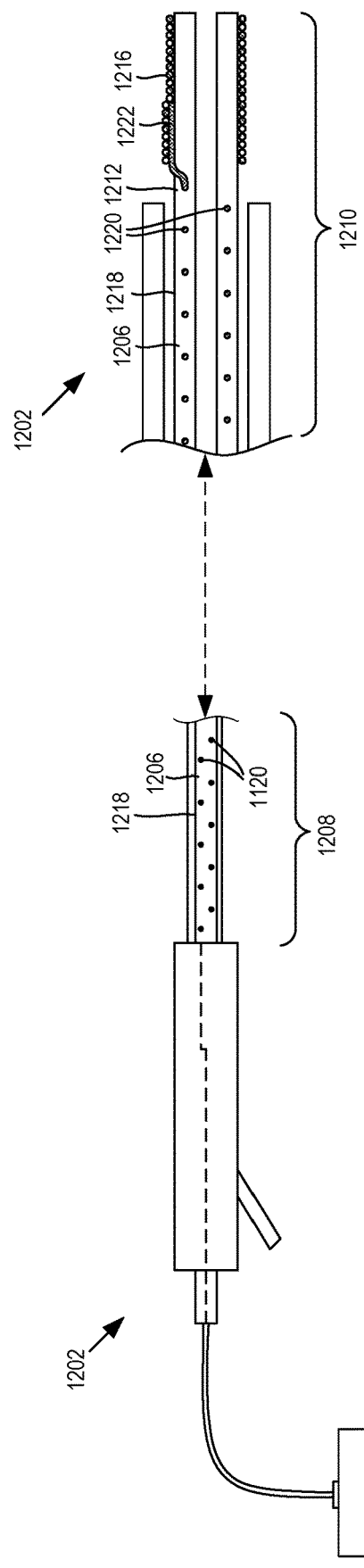
FIG. 12 is a partial cross-sectional side view of an eleventh example electrosurgical device configured to gain access into a pseudocyst that includes a conductive coil disposed over a distal end of a separate elongate conductive member in a coiled configuration while embedded in a body of an elongate tubular member.

Referring to FIG. 12, a first conductive coil 1220 may be embedded in a body 1212 of an elongate tubular member 1206, and while embedded, longitudinally extend from a proximal portion 1208 to a distal portion 1210. At the distal portion 1210, a distal portion 1222 of the first conductive coil 1220 may extend from the body 1212 to outside the elongate tubular member 1206, where the distal portion 1222 may be disposed on an outer surface 1228. A second conductive coil 1216 may cover and be fixedly attached and electrically connected to the distal portion 1222 of the first conductive coil 1220.

Figure 13:
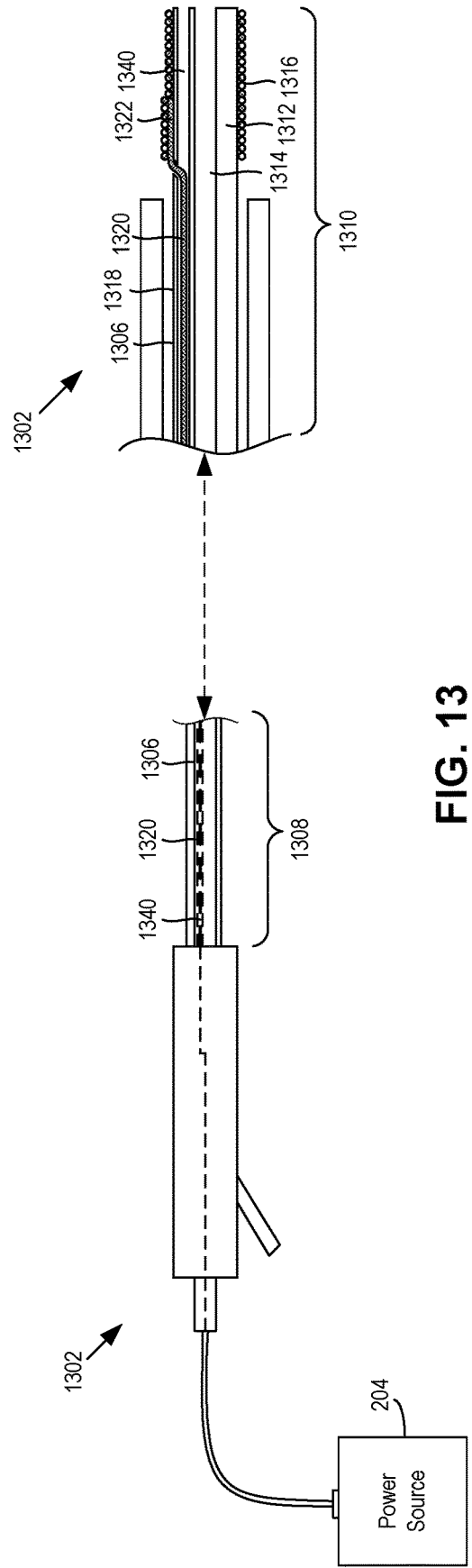
FIG. 13 is a partial cross-sectional side view of a twelfth example electrosurgical device configured to gain access into a pseudocyst that includes a conductive coil disposed over a distal end of a separate elongate conductive member longitudinally extending in a lumen of an elongate tubular member.

Referring to FIG. 13, an elongate tubular member 1306 may include a wireguide lumen 1314 and a second lumen 1340 longitudinally extending in a body 1312 from a proximal portion 1308 to a distal portion 1310. An elongate conductive member 1320 may be disposed and longitudinally extend in the second lumen 1340 from the proximal portion 1308 to the distal portion 1310. At the distal portion 1310, a distal portion 1322 of the elongate conductive member 1320 may exit the second lumen 1340 and extend to outside the elongate tubular member 1306, where the distal portion 1322 may be disposed on an outer surface 1318 of the elongate tubular member 1306. A conductive coil 1316 may cover and be fixedly attached and electrically connected to the distal portion 1322 of the elongate conductive member 1320.

Figure 14:
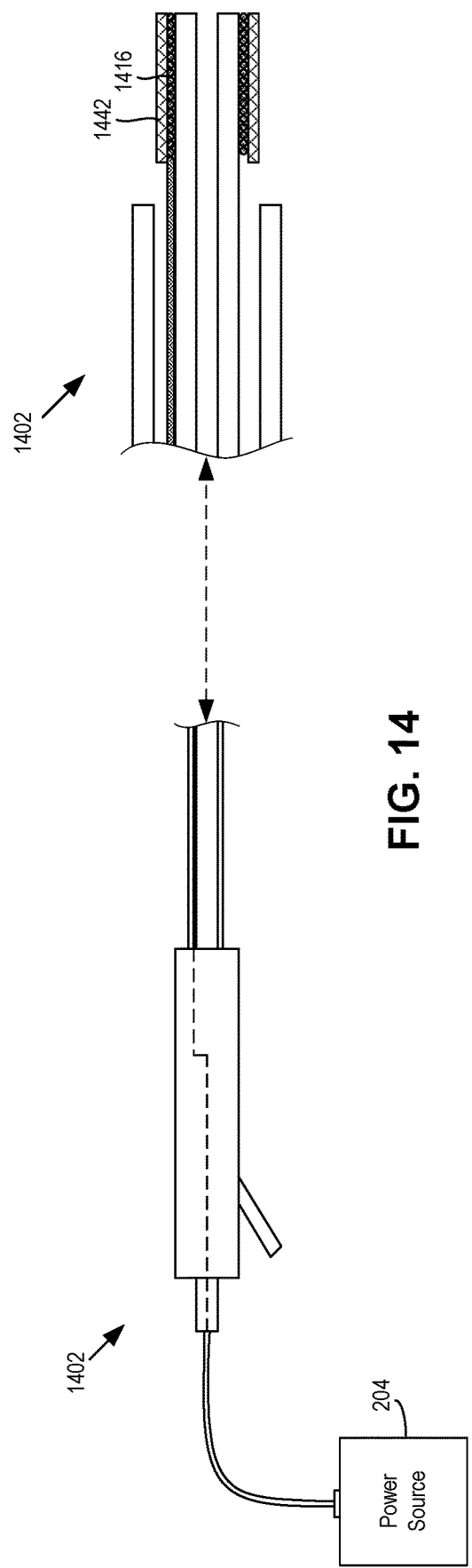
FIG. 14 is a partial cross-sectional side view of a thirteenth example electrosurgical device configured to gain access into a pseudocyst that includes a conductive coil integral with an elongate conductive member longitudinally extending on an outer surface of an elongate tubular member, and a conductive cannula disposed over the conductive coil.

Referring to FIG. 14, a partial cross-sectional side view of a thirteenth example embodiment of an electrosurgical device 1402 in electrical connection with the power source 204 is shown. The electrosurgical device 1402 may be similar to the fifth example embodiment 602 of FIG. 6, except that the thirteenth example embodiment 1402 may further include a conductive cannula 1442 disposed over and/or about the conductive coil 1416. The conductive cannula 1442 may be fixedly attached and electrically connected to the conductive coil 1416 through a mechanical mechanism (e.g., crimping) and/or a thermal mechanism (e.g., welding).

The thirteen embodiments shown in FIGS. 2-14 are exemplary and other configurations including various combinations of the above-described features may be possible. For example, the sixth, seventh, and eighth example embodiments 702, 802, 902 of FIGS. 7, 8, and 9, respectively, may similarly include a conductive cannula disposed over a conductive coil to form a conductive tubular distal tip, similar to the thirteenth example embodiment shown in FIG. 14. Other configurations may be possible. As another example, each of the embodiments in FIGS. 2-14 are shown as including the outer elongate tubular member 238. However, alternative configurations for any of these embodiments may not include the outer elongate tubular member 238. For these alternative configurations, the handle assembly 224 may still be operative to maneuver the single tubular member and the conductive tubular distal tip and to deliver electrical current to the conductive distal tip, but may not necessarily be adapted to move coaxial inner and outer tubular members relative to each other.

A method of gaining access by creating an opening into an anatomical structure that is in, adjacent to, and/or accessible from a treatment site of a patient is described with reference to FIGS. 15A-15E. The method described with reference to these figures identifies a treatment site 1500 as being an area of a gastrointestinal (GI) tract, and an anatomical structure 1502 as being a pseudocyst that is outside and adjacent to the GI tract and pushing up against a wall 1504 of the GI tract. However, the method may be similarly applied to gaining access into anatomical structures other than pseudocysts and/or anatomical structure that are located in other areas of or within a body of a patient, including those that are in, adjacent to, and/or accessible from the GI tract. An example anatomical structure may be the papilla of Vater, which is an exit hole for the biliary tree that delivers secretions from organs such as the liver, gallbladder, and pancreas, into the duodenum. Other anatomical structures may be possible. For some anatomical structures, such as a pseudocyst, creating the opening may include making or creating an incision in the anatomical structure. For other anatomical structures, such as the papilla of Vater, the anatomical structure may already have an initial opening. However, the initial opening is too small and/or restrictive for access into an area beyond the anatomical structure, such as access into the biliary tree from the duodenum. For these other anatomical structures, creating the opening includes enlarging the initial or pre-existing opening by performing the cutting. After the opening is created, a subsequent act may be performed that is related to the purpose of gaining access into the anatomical structure. For example, with pseudocysts, a drainage device, such as a stent, may be inserted into the opening in order to drain the stent. As another example, a medical device (e.g., forceps or a basket) maybe inserted into the opening in order to remove stones (e.g., gallstones), or a visualization device (e.g., a camera or image sensor) may be inserted through the opening for visual diagnostic purposes. Other actions after the opening is created may be performed. Also, the method is described as being performed using the first embodiment 202 of the electrosurgical device shown and described with reference to FIG. 2, although any of the other embodiments may be similarly used to perform the method.

Figure 15A:
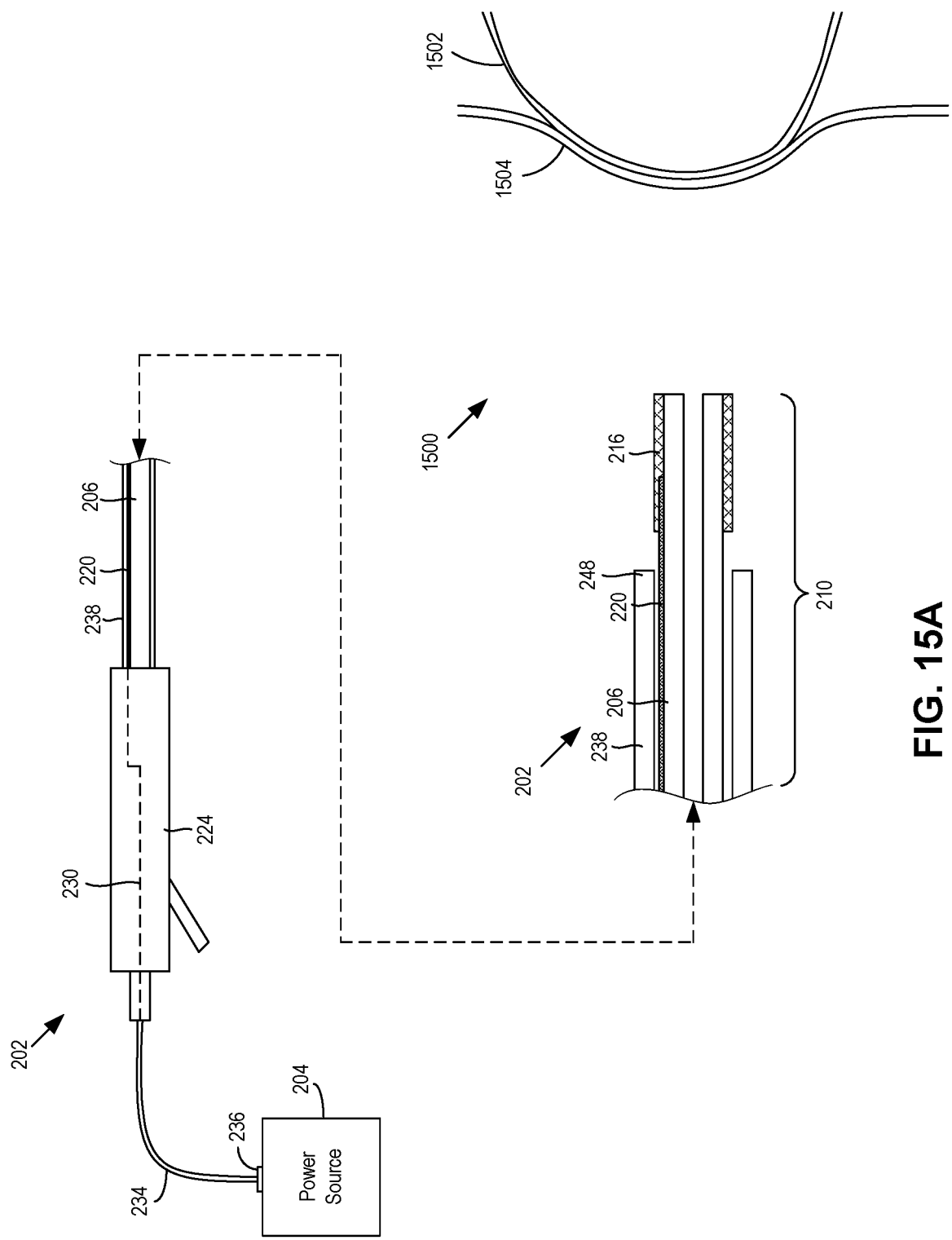
FIG. 15A is a side view of the first example electrosurgical device of FIG. 2, with its distal portion being delivered to a treatment site near a pseudocyst.

Referring to FIG. 15A, the distal portion 210 of the elongate tubular member 206 may be delivered to a treatment site 1500 within a patient, such as an area of the patient's GI tract. Although not shown, the distal portion 210 may be delivered to the treatment site 1500 by being moved through a channel or lumen of an endoscope. At the treatment site 1500, a pseudocyst 1502, such as a pancreatic pseudocyst, may be pushing up against a wall 1504 (such as a transgastric or transduodenal wall) of an internal organ associated with the GI tract, such as the stomach or the duodenum. In some methods, the pseudocyst 1502 may be identified by identifying a bulge in the wall 1504 using a visualization device (not shown). In some methods, while being delivered to the treatment site 1500, the conductive cannula 216 may be disposed within the outer elongate tubular member 238. At the treatment site 1500, the handle assembly 224 may be operated to move the conductive cannula 216 distally past the distal end 248 of the outer elongate tubular member 238 so that the conductive cannula 216 is exposed to the tissue at the treatment site 1500, which is shown in FIG. 15A. Alternatively, where an electrosurgical device not including the outer elongate tubular member 238 is used to perform the method, this operation of the handle assembly 224 to expose the conductive cannula 216 may not be performed.

In addition, when the conductive cannula 216 is at the treatment site 1500, the conductive cannula 216 may be electrically activated by activating the power source 204.

When activated, the power source 204 may deliver electrical current from the output port 236, through the cabling 234, through the conductive coupling component 230, through the elongate conductive member 220, and to the conductive cannula 216. Power associated with the electrical current that is delivered may be in a range of between 80-120 Watts, although other power settings may be possible. Also, the frequency of the electrical current may be a frequency used for electrosurgery, which may be in the radio frequency (RF) range. An example frequency range may include 350 kiloHertz (kHz) to 4 Megahertz (MHz), although other frequencies used for electrosurgery outside of this range may be possible.

Figure 15B:
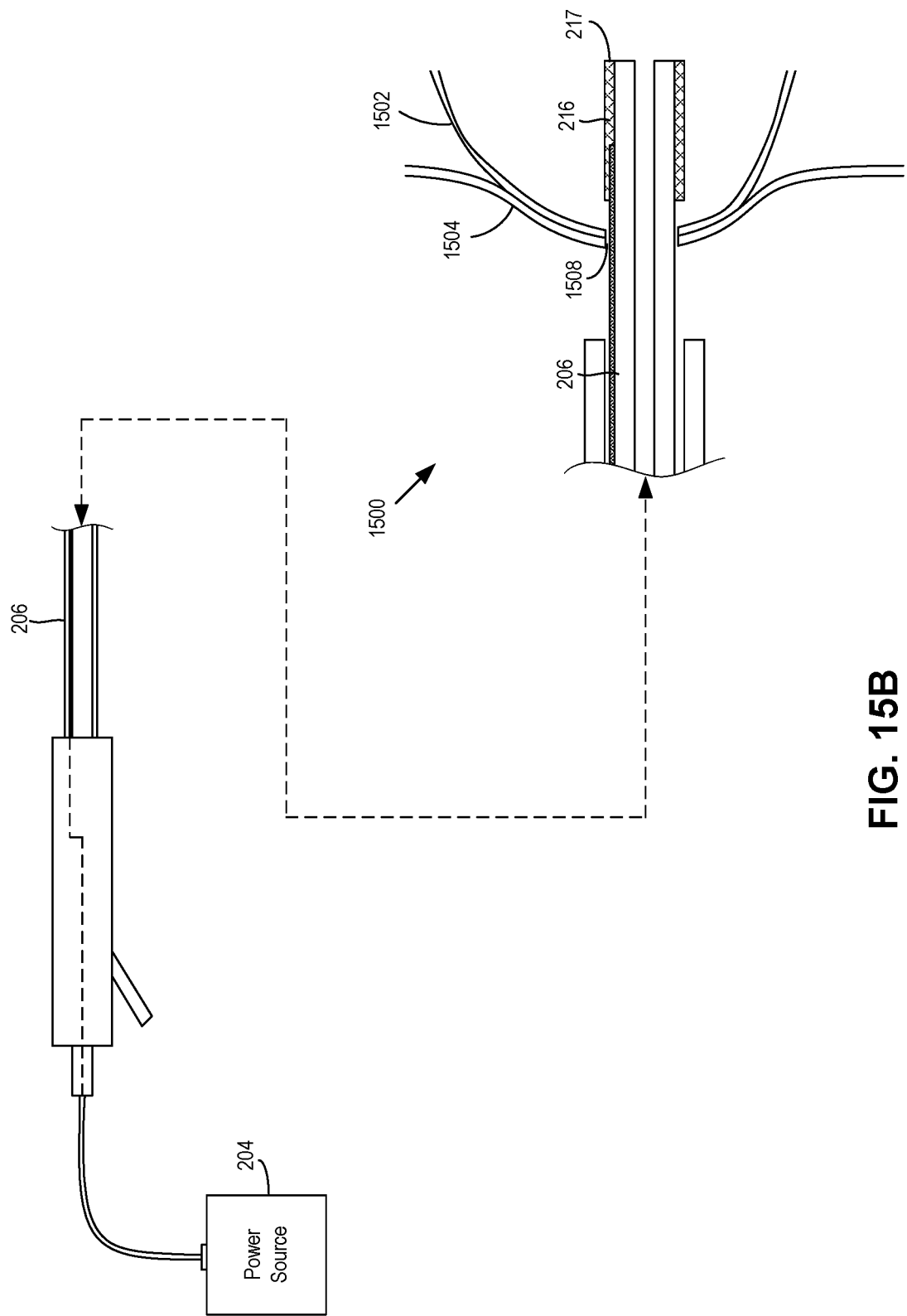
FIG. 15B is a side view of the first example electrosurgical device of FIG. 2, with its distal portion creating an incision in a wall and the pseudocyst of FIG. 15A.

Referring to FIG. 15B, the elongate tubular member 206 and the electrically activated conductive cannula 216 may be distally advanced so that the conductive cannula 216, including its distal end 217, contacts and cuts into the bulging part of the wall 1504. The tubular member 206 and the conductive cannula 216 may continue to be distally advanced so that the conductive cannula 216 further cuts into the pseudocyst 1502 to make an opening, such as an incision, 1508. (As previously described, other anatomical structures may already include an opening 1508 before the cutting, such that creating the opening may include enlarging the existing opening 1508). As shown in FIG. 15B, at this point during the procedure, a distal portion of the tubular member 206 and conductive cannula 216 may have gained access into and be disposed in the pseudocyst 1502. For other methods involving treatments sites other than the one shown in FIGS. 15A-15E, where there is no wall 104 separating the anatomical structure from the conductive cannula 216 (e.g., where the anatomical structure is in the treatment site (such as on or attached to the wall 104 and protruding into the GI tract), the cutting operation may not involve cutting into the wall 104, and instead may involve cutting directly into the anatomical structure.

Figure 15C:
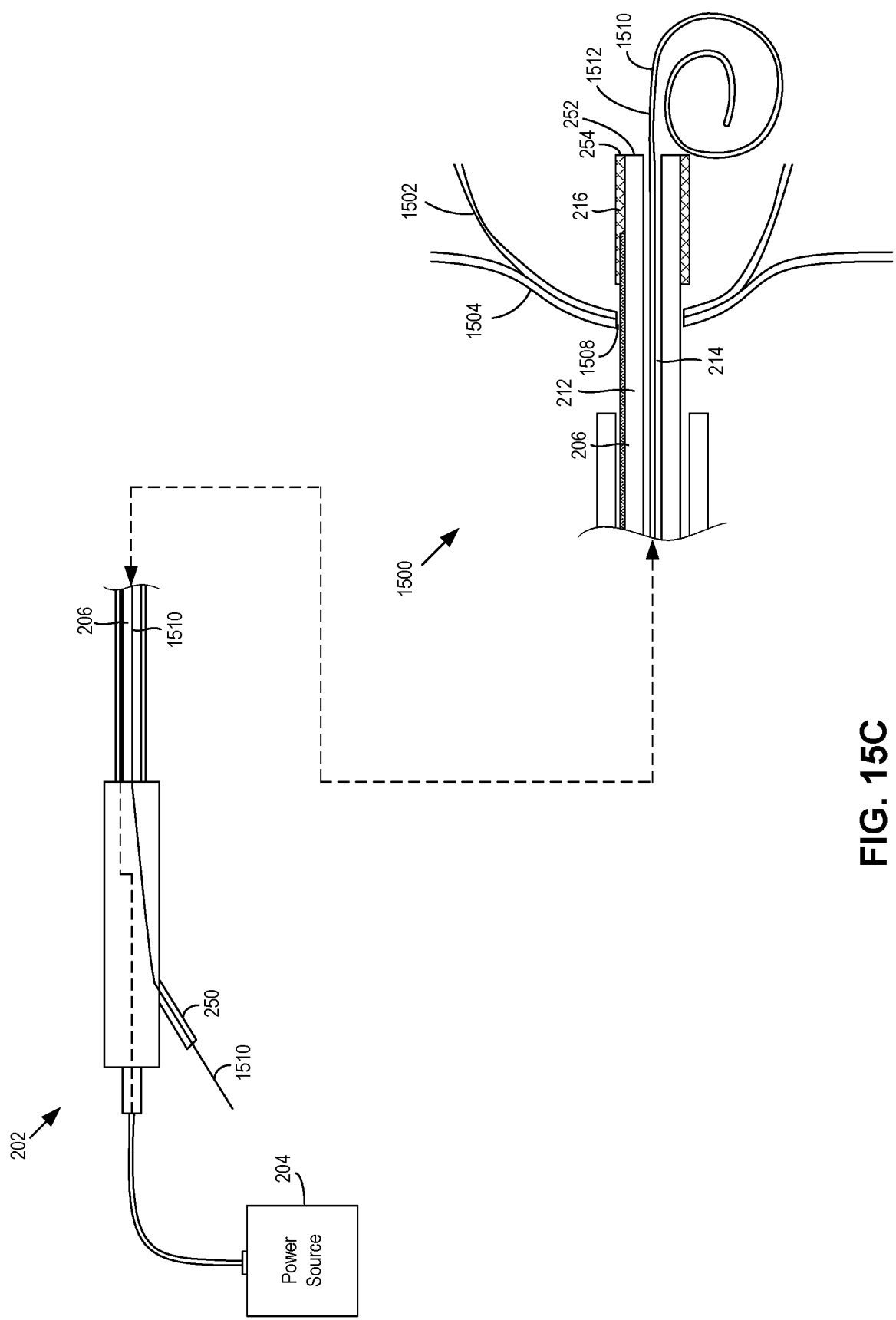
FIG. 15C is a side view of the first example electrosurgical device of FIG. 2, with a distal portion of a wireguide being inserted into the pseudocyst of FIG. 15A.

Referring to FIG. 15C, with the tubular member 206 and conductive cannula 216 having gained access into and disposed in the pseudocyst 1504, a wireguide 1510 may be distally advanced through the wireguide lumen 214 until a sufficient amount of a distal portion 1512 of the wireguide 1510 is distally advanced past distal ends 252, 254 of the tubular member 206 and the cannula 216 inside the psuedocyst 1502. FIG. 15C shows the distal portion 1512 having curled inside the pseudocyst 1502 when past the distal end 252 and outside of the tubular member 206. As shown in FIG. 15C, the wireguide 1510 may be inserted into the wireguide portion 250 of the handle assembly 224 and then advanced into the wireguide lumen 214 from the handle assembly 224. Also, in some example methods, the conductive cannula 216 may be electrically deactivated from the power source 204 prior to the distal portion 1512 being advanced past the distal ends 252, 254 of the tubular member 206 and the conductive cannula 216 in order to ensure that the distal portion 1512 is not electrically activated. During the operation, if the physician determines that further cutting with the conductive cannula 216 is to be performed, the distal portion 1512 may be withdrawn back to within the wireguide lumen 214, where the body 212 may electrically insulate the distal portion 1512 from the electrically activated conductive cannula 216. Alternatively, the distal portion 1512 and the conductive cannula 216 may be moved relative to each other within the pseudocyst 1502 to be a sufficient distance away from each other so that when the cannula 216 is electrically activated for further cutting, the wireguide 1510 is not also electrically activated. Electrically activating the wireguide 1510 may be undesirable as it could possible harm to the patient and/or the physician maneuvering the wireguide 1510.

Figure 15E:
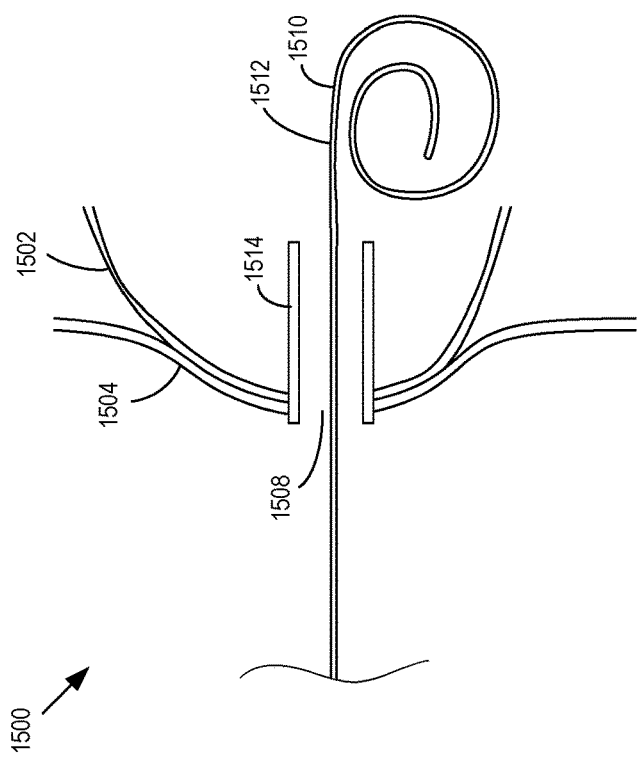
FIG. 15E is a partial cross-sectional side view of a drainage device being positioned in the created incision.
Figure 15D:
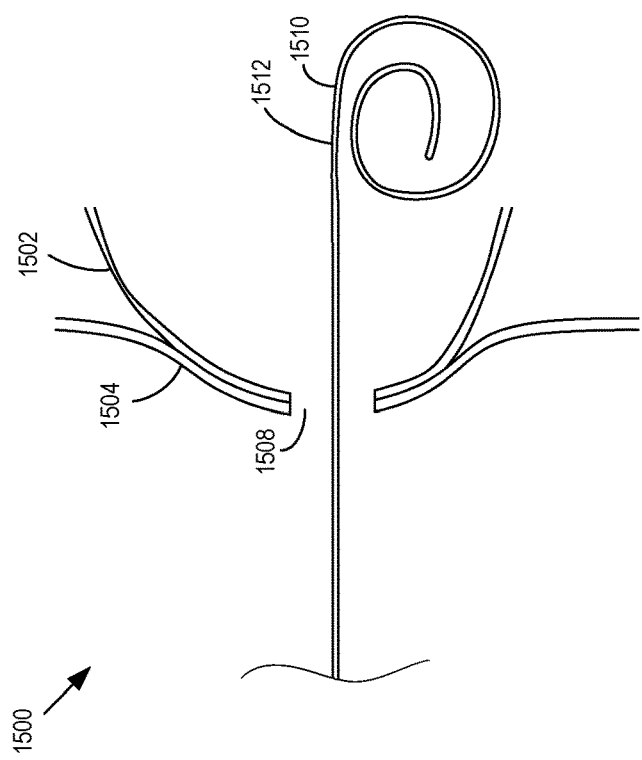
FIG. 15D is a side view of the distal portion of the wireguide of FIG. 15C being kept inside the pseudocyst of FIG. 15A, while a distal portion of the first example electrosurgical device of FIG. 2 has been withdrawn from the treatment site.

Referring to FIG. 15D, after the distal portion 1512 of the wireguide 1510 is positioned in the pseudocyst 1502 and cutting with the conductive cannula 216 is complete, the conductive cannular 216 and the distal portion 210 of the tubular member 206 may be withdrawn from inside the pseudocyst 1502 and further to outside the patient, while wireguide 1510 remains in the patient, with the distal portion 1512 disposed in the pseudocyst 1502. Referring to FIG. 15E, a stent or other drainage device 1514 may be inserted onto the wireguide 1510 outside of the patient and distally advanced within the patient to the treatment site 1500. The drainage device 1514 may be further advanced and positioned in the opening 1508, where at least a portion of the drainage device 1514 is disposed within the pseudocyst 1502.

The drainage device 1504 may have an outer diameter of less than 10 French. As described above, the conductive cannula 216 may have an outer diameter in between 5 French and 10 French, such as 6 French, which may provide a suitable size of the opening 1508 for the drainage device 1514 to be securely held and/or maintained inside the pseudocyst 1502. Also, in the example method described with reference to FIGS. 15A-15E, only a single conductive tubular element affixed to a single tubular member is electrically activated to create the opening 1508. That is, a second conductive tubular element affixed to a second tubular member is not used to make the opening 1508. With reference to FIGS. 15A-15E, the single conductive tubular element is the cannula 216, although in other methods, the single conductive tubular element may be a coil or a combination of a cannula and a coil, as shown in described with reference to FIGS. 3-14.

After the drain device 1514 is inserted into the opening 1508, the wireguide 1510 may be removed from the treatment area 1500 and drainage of the pseudocyst 1502 may be performed via the drainage device 1514.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method of gaining access into a pseudocyst, the method comprising:
   delivering an electrosurgical device separate from an endoscope to a treatment site, the electrosurgical device delivered to the treatment site via a channel or lumen of the endoscope, the electrosurgical device comprising an outer elongate tubular member, an inner elongate tubular member, and a conductive tubular element disposed on an outer surface of the inner elongate tubular member, wherein an outer diameter of the conductive tubular element is greater than five French (one and two-thirds millimeters) and less than ten French (three and one-third millimeters);

electrically activating the conductive tubular element; and creating an opening in the pseudocyst by initially cutting the pseudocyst with the electrically activated conductive tubular element and moving the electrically activated conductive tubular element into the pseudocyst while leaving the outer elongate tubular member outside of the pseudocyst, wherein the pseudocyst does not have any opening from cutting prior to the initial cutting with the electrically activated conductive tubular element.

2. The method of claim 1, wherein creating the opening comprises creating an incision in the pseudocyst.

3. The method of claim 1, wherein creating the opening comprises creating the opening with only the electrically activated conductive tubular element.

4. The method of claim 1, wherein initially cutting into the pseudocyst comprises distally advancing a distal end of the conductive tubular element into the pseudocyst while the conductive tubular element is electrically activated.

5. The method of claim 1, wherein initially cutting into the pseudocyst comprises initially cutting into the pseudocyst with a side surface defining a distal end of the conductive tubular element.

6. The method of claim 1, further comprising: after creating the opening, positioning a drainage device in the opening for drainage of the pseudocyst.

7. The method of claim 6, further comprising:

before positioning the drainage device in the opening, distally advancing a distal portion of a wireguide through the opening to within the pseudocyst; and distally advancing the drainage device over the wireguide to the treatment site in order to position the drain device in the opening.

8. The method of claim 7, wherein distally advancing the distal portion of the wireguide comprises distally advancing the distal portion through a wireguide lumen of the elongate tubular member.

9. The method of claim 1, wherein the conductive tubular element comprises at least one of a conductive cannula or a conductive coil.

10. The method of claim 1, further comprising:

delivering electrical current in a range of 80-120 Watts to the conductive tubular element while the conductive tubular element is cutting into the pseudocyst to create the opening.

11. The method of claim 1, wherein the inner elongate tubular member comprises a body and a wireguide lumen longitudinally extending through the body, the body comprising an insulating material that electrically insulates the wireguide lumen from the conductive tubular element.

12. The method of claim 1, wherein the treatment site is in a gastrointestinal tract of the patient.

13. The method of claim 12, wherein the pseudocyst is adjacent a wall of the gastrointestinal tract, the method further comprising:

cutting into the wall before cutting into the pseudocyst in order to create the opening.

14. The method of claim 13, wherein the pseudocyst is adjacent the wall outside the gastrointestinal tract.

* * * * *